(12) United States Patent
Nakatani et al.

(10) Patent No.: US 8,828,360 B2
(45) Date of Patent: Sep. 9, 2014

(54) HAIR STYLING COMPOSITIONS WITH IMPROVED CLARITY AND HUMIDITY RESISTANCE

(75) Inventors: Alan Isami Nakatani, Lansdale, PA (US); Curtis Schwartz, Ambler, PA (US); Miao Wang, Schwenksville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 13/196,198

(22) Filed: Aug. 2, 2011

(65) Prior Publication Data

US 2012/0039819 A1    Feb. 16, 2012

Related U.S. Application Data

(60) Provisional application No. 61/401,239, filed on Aug. 10, 2010.

(51) Int. Cl.
| | |
|---|---|
| *A61K 8/00* | (2006.01) |
| *A61K 9/00* | (2006.01) |
| *A61K 8/18* | (2006.01) |
| *A61K 8/72* | (2006.01) |
| *A61K 8/81* | (2006.01) |
| *A61Q 5/00* | (2006.01) |
| *A61Q 5/06* | (2006.01) |
| *A61K 8/86* | (2006.01) |
| *A61K 8/41* | (2006.01) |

(52) U.S. Cl.
CPC ............... *A61Q 5/06* (2013.01); *A61K 8/8152* (2013.01); *A61K 8/86* (2013.01); *A61K 8/41* (2013.01)
USPC ....... 424/47; 424/70.16; 424/70.1; 424/70.11

(58) Field of Classification Search
None
See application file for complete search history.

(56) References Cited

U.S. PATENT DOCUMENTS

| | | | |
|---|---|---|---|
| 4,192,861 A | 3/1980 | Micchelli et al. | |
| 4,315,910 A | 2/1982 | Nowak, Jr. et al. | |
| 5,164,177 A | 11/1992 | Bhatt et al. | |
| 5,965,146 A * | 10/1999 | Franzke et al. | 424/401 |
| 2009/0252689 A1 * | 10/2009 | Collin et al. | 424/47 |

FOREIGN PATENT DOCUMENTS

GB      2291893 A      2/1996

* cited by examiner

*Primary Examiner* — Brian-Yong Kwon
*Assistant Examiner* — Mark V Stevens
(74) *Attorney, Agent, or Firm* — Edward L. Brant

(57) ABSTRACT

The present invention provides a hair styling composition comprising (a) 1% to 10% by weight of at least one polymer comprising, as polymerized units, one or more monomers having at least one acid-functional group; (b) 99% to 90% by weight of a solvent mixture comprising: (i) 5% to 100% by weight of at least one volatile organic solvent; (ii) 95% to 0% by weight of water, and (iii) 0% to 80% by weight of at least one propellant; and (c) a neutralizer, wherein the mole ratio of said neutralizer to the acid-functional groups on said polymer (a) is from 0:1 to 1.2:1, and the neutralizer comprises: (i) 10% to 30% neutralization of the acid group of the polymer by tetrabutylammonium hydroxide, and (ii) 90% to 70% neutralization of the acid group of the polymer by aminomethyl propanol. More particularly, the polymer (a) may comprise, as polymerized units, (i) 30% to 75% by weight of one or more monomer that has refractive index of 1.490 or higher, (ii) 1% to 30% by weight of one or more acid-functional monomer, and (iii) 5% to 69% by weight of one or more additional monomer. The hair styling composition of the present invention has improved clarity and humidity resistance.

11 Claims, No Drawings

HAIR STYLING COMPOSITIONS WITH IMPROVED CLARITY AND HUMIDITY RESISTANCE

This application claims the benefit of priority under 35 U.S.C. §119(e) of U.S. Provisional Patent Application No. 61/401,239 filed on Aug. 10, 2010.

FIELD OF THE INVENTION

The present invention relates to hair spray compositions having improved clarity while maintaining other properties such as hold and shine.

BACKGROUND

Hair styling compositions are desired that provide both good hold (i.e., the ability to hold hair in place) and good shine (i.e., the ability to give hair a shiny appearance). Additionally, clarity (translucent appearance) of the hair styling composition prior to application is aesthetically important to consumers.

Typically, hair styling compositions include one or more polymers which serve as the hair fixative. While there are many polymers that provide good hold in hair styling compositions, some of them negatively impact other properties such as shine or clarity.

Hair styling compositions also typically include an aqueous solvent which is a mixture of water and one or more volatile organic solvents. The class of volatile organic compounds (VOCs) which are liquid at 25° C. and one atmosphere pressure are generally useful as volatile organic solvents in hair spray compositions. Because hair styling compositions are sometimes sprayed, it is desirable that any polymers used in the composition dissolve fully in the aqueous solvent. Further, for proper spraying, it is desirable that a solution of any polymers used in the composition should have viscosity that is not too high.

Where a hair styling composition is to be applied in an aerosol spray, the aqueous solvent also includes one or more propellants, which may be volatile non-organic compounds or VOCs and are gaseous at 25° C. and one atmosphere pressure. For example, without limitation, it is known to use carbon dioxide, propane, isobutane, dimethyl ether and tetrafluoroethane, among other materials, as the aerosol propellant for such compositions.

It is also desirable that the hair styling composition be stable (i.e., that none of the ingredients settles while the composition is in storage). It is known that as the volatile organic compound (VOC) content of a composition containing certain polymers increases, a haze appears, and increases, in the composition, due to insolubility and precipitation of the polymer from aqueous solvent. This haze is aesthetically unpleasing to consumers.

Thus, selecting the types and proportions of ingredients for hair styling compositions is very important and can be difficult. It is desired to provide polymers which have good hold characteristics, without negatively impacting the levels of shine and clarity in hair styling compositions. Typical high VOC-containing hair fixative polymers can result compositions that are hazy. The present invention is believed to improve polymer compatibility in such compositions, thereby resulting in improved clarity (i.e., reduced haze).

One approach to improving the water solubility of carboxylated vinyl polymeric hair spray resins in alcohol hydrocarbon propellant systems has been to neutralize at least a portion of the available carboxyl functionalities of the resins, as described in U.S. Pat. No. 4,192,861, using alkaline reagents.

U.S. Pat. No. 4,315,910 describes aerosol hair spray compositions used in aerosol metal containers that contain polymer, including, for example, styrene/maleic anhydride polymers, as well as carbon dioxide or hydrocarbon-alcohol propellants and 1-15% by weight water. It is asserted in U.S. Pat. No. 4,315,910 that addition of the water to this composition improved shelf stability and solubility of the polymer in these compositions compared to anhydrous compositions using carbon dioxide or hydrocarbon-alcohol in aerosol metal containers.

It is also known to improve the clarity of non-aerosol, gel hair styling compositions containing silicone grafted co-polymers by neutralization with organic or inorganic neutralizer or mixtures thereof. GB 2 291 893 A describes an aqueous/alcohol hair styling gel containing a silicone-containing polycarboxylic acid polymer and selected organic neutralizing agents that is claimed to have further improved clarity as well as non-sticky in-use feel and easy brush-out characteristics.

An object of the present invention was to identify neutralizing agents which render the polymers more compatible with the VOCs used in hair styling compositions.

SUMMARY OF THE INVENTION

The present invention provides a hair styling composition comprising:
(a) 1% to 10% by weight of at least one polymer, based on the total weight of said polymer (a) and a solvent mixture (b), said at least one polymer comprising, as polymerized units, one or more monomers having at least one acid-functional group;
(b) 99% to 90% by weight of said solvent mixture, based on the total weight of said polymer (a) and said solvent mixture (b), said solvent mixture comprising:
  (i) 5% to 100% by weight of at least one volatile organic solvent, based on the total weight of said solvent mixture;
  (ii) 95% to 0% by weight of water, based on the total weight of said solvent mixture, and
  (iii) 0% to 80% by weight of at least one propellant, based on the total weight of said solvent mixture; and
(c) a neutralizer, wherein the mole ratio of said neutralizer to the acid-functional groups on said polymer (a) is from 0:1 to 1.2:1, said neutralizer comprising:
  (i) 10% to 30% neutralization of the acid group of the polymer by tetrabutylammonium hydroxide, and
  (ii) 90% to 70% neutralization of the acid group of the polymer by aminomethyl propanol.

In one embodiment, the polymer (a) has a turbidity of 10 NTU or less in a solution with 12% or less, by weight, polymer solids, based on the total weight of the solution.

In another embodiment, the hair styling composition has a decrease in storage modulus of no more than 50%, from 0% to 30% relative humidity. Alternatively, the hair styling composition may have a decrease in storage modulus of no more than 75%, from 0% to 60% relative humidity.

In still another embodiment of the hair styling composition of the present invention, the polymer (a) may comprise, as polymerized units, (i) 30% to 75% by weight, based on the weight of said polymer, one or more monomer that has refractive index of 1.490 or higher, (ii) 1% to 30% by weight, based on the weight of said polymer, one or more acid-functional monomer, and (iii) 5% to 69% by weight, based on the weight of said polymer, one or more additional monomer.

Furthermore, the monomer (i) may comprise one or more vinyl aromatic monomers. Independently, the monomer (iii) may comprise one or more hydroxyalkyl(meth)acrylate. The polymer may be selected from the group consisting of: butyl acrylate/ethyl acrylate/methacrylic acid copolymers, octylacrylamide/acrylate/butylaminoethyl-methacrylate copolymers, methacryloyl ethyl-betaine/methacrylate copolymers, methacrylic acid/methacrylic ester copolymer, acrylates/hydroxyesters acrylates copolymer, methacrylic acid/acrylic acid ester copolymers, vinyl acetate/crotonic acid copolymer, vinyl acetate/crotonic acid/vinyl neodecanoate, acrylates copolymer, methacrylates/acrylates copolymer/amine salt, acrylates/methacrylate polymers, acrylates/acrylamide copolymer, acrylates/succinates/hydroxyacrylates copolymer, acrylates/t-butylacrylamide copolymer, acrylates/$C_{1-2}$ succinates/hydroxyacrylates copolymer, acrylamide/sodium acryloyldimethyltaurate/acrylic acid polymer, and mixtures thereof.

The present invention also provides a method for styling hair comprising the steps of placing said hair in a desired configuration and applying the hair styling composition described above to the hair.

DETAILED DESCRIPTION

A "hair styling composition" as used herein is a composition that may be used on hair to hold the hair in a particular shape or configuration. Such compositions typically contain various polymeric resins, gums, and/or adhesive agents designed to impart desirable properties to the compositions and, ultimately, to hair upon which the compositions are applied. The polymers are used for a variety of purposes including, for example, one or more of hair holding, improving volume, improving appearance, and imparting desirable feel properties. Much of the ability of hair styling compositions to hold the hair in a particular shape results from one or more polymer used in the compositions. Hair styling compositions include, for example, hair sprays, styling gels, spray gels and mousses.

A "polymer," as used herein and as defined by F W Billmeyer, J R. in *Textbook of Polymer Science*, second edition, 1971, is a relatively large molecule made up of the reaction products of smaller chemical repeat units.

Polymer molecular weights can be measured by standard methods such as, for example, size exclusion chromatography (SEC, also called gel permeation chromatography or GPC). Generally, polymers have weight-average molecular weight (Mw) of 1,000 or more. Some polymers are characterized by Mn, the number-average molecular weight.

As used herein "weight of polymer" means the dry weight of polymer.

Molecules that can react with each other to form the repeat units of a polymer are known herein as "monomers." One example of a class of monomers that are useful in the present invention are, for example, ethylenically unsaturated monomers (i.e., monomers that have at least one carbon-carbon double bond). Typical ethylenically unsaturated monomers have molecular weight of less than 500. Among such monomers are, for example, vinyl monomers. Some suitable vinyl monomers include, for example, styrene, substituted styrenes, dienes, ethylene, ethylene derivatives, and mixtures thereof. Ethylene derivatives include, for example, unsubstituted or substituted versions of the following: vinyl acetate, acrylonitrile, (meth)acrylic acids, (meth)acrylates, (meth)acrylamides, vinyl chloride, halogenated alkenes, and mixtures thereof. As used herein, "(meth)acrylic" means acrylic or methacrylic; "(meth)acrylate" means acrylate or methacrylate; and "(meth)acrylamide" means acrylamide or methacrylamide. "Substituted" means having at least one attached chemical group such as, for example, alkyl group, alkenyl group, vinyl group, hydroxyl group, carboxylic acid group, other functional groups, and combinations thereof.

A polymer that is made by polymerizing a certain monomer, either alone or with other monomers, is said herein to include that monomer as a polymerized unit.

As used herein, "normal boiling point" of a compound is the boiling point at one atmosphere pressure. As used herein, a "volatile" compound is a compound with normal boiling point of 250° C. or lower. As used herein, "INCI" is the International Nomenclature of Cosmetic Ingredients.

The "humidity resistance" of a hair styling composition is measured as the "storage modulus decrease" of a hair styling composition. As used herein, the "storage modulus decrease" means the percent decrease in the storage modulus of a given hair styling composition, starting at 0% relative humidity and ending at the specified relative humidity. For example, a hair styling composition that has a storage modulus decrease of 50% at 30% relative humidity, means that the storage modulus of that composition at 0% relative humidity decreased by 50% when the relative humidity was raised to 30%.

The "clarity" of a particular polymer used in a hair styling composition may be measured by its turbidity, in units of Nephelometric Turbidity Units (NTU) as described in detail hereinafter. A polymer may be said to have "enhanced clarity" when it has turbidity of 10 NTU or lower in a solution with 12% polymer solids or less (by weight based on the weight of the solution).

As used herein, an "organic" compound is any compound that contains one or more carbon atoms except for those carbon-containing compounds that are generally accepted to be inorganic compounds. Examples of carbon-containing compounds that are generally accepted to be inorganic compounds include the following: carbon oxides (such as, for example, carbon dioxide), carbon disulfide, metallic cyanides, metallic carbonyls, phosgene, carbonyl sulfide, metallic carbonates, and metallic bicarbonates.

In some embodiments, hair styling composition of the present invention is suitable as a hair spray. In some of such embodiments, hair styling composition is suitable as a pump spray or as an aerosol spray. In some of such embodiments, hair styling composition is suitable as an aerosol spray.

Hair styling composition of the present invention comprises at least one polymer comprising, as polymerized units, one or more monomers having at least one acid-functional group (known herein as "polymer (a)").

In some embodiments, polymer (a) contains one or more vinyl polymer. In some embodiments, every polymer (a) in the hair styling composition is a vinyl polymer. As used herein, a vinyl polymer is a polymer made by polymerization of vinyl monomers. In some embodiments, a vinyl polymer is made by free radical polymerization of vinyl monomers.

Independent of the composition of polymer (a), in some embodiments, one or more polymer (a) is used that has Mw of 25,000 or higher, or 50,000 or higher. Independently, in some embodiments, one or more polymer (a) is used that has Mw of 300,000 or lower, or 150,000 or lower. Independently, in some embodiments, every polymer (a) has Mw of 25,000 to 300,000.

Polymer (a) of the present invention contains polymerized units of one or more monomer (known herein as "monomer (i)") that has refractive index of 1.490 or higher. Refractive index of a monomer can be measured, for example, by ASTM Standard D1218-02, at 25° C. In some embodiments, monomer (i) contains one or more monomer with refractive index of 1.500 or higher; or 1.530 or higher. In some embodiments, every monomer (i) is a monomer with refractive index of 1.530 or higher.

In some embodiments, monomer (i) contains one or more vinyl monomer. In some embodiments, monomer (i) contains one or more vinyl aromatic monomer. A vinyl aromatic monomer is a monomer that contains one or more carbon-carbon double bond and one or more aromatic ring. Suitable vinyl aromatic monomers include, for example, monomers with benzyl groups, monomers with phenyl groups, styrene, derivatives of styrene (such as, for example, alpha-methyl styrene), and mixtures thereof. In some embodiments, every monomer (i) is a vinyl aromatic monomer. In some embodiments, monomer (i) comprises one or more of styrene, alpha-methyl styrene, or a mixture thereof. In some embodiments, every monomer (i) is selected from styrene, alpha-methyl styrene, and mixtures thereof.

Mixtures of suitable monomers (i) are also suitable.

The amount of polymerized units of monomer (i) in the polymer (a) of the present invention is 30% to 75% by weight, based on the weight of the polymer (a). In some embodiments, the amount of polymerized units of monomer (i) is 35% or more, or 39% or more, by weight, based on the weight of the polymer. In some embodiments, the amount of polymerized units of monomer (i) is 65% or less, or 55% or less, by weight, based on the weight of the polymer.

Polymer (a) of the present invention additionally contains one or more polymerized unit of one or more monomer (herein called "monomer (ii)") that has at least one acid-functional group. Suitable acid-functional groups include, for example, sulfonic acid groups and carboxylic acid groups. The acid-functional groups may be in neutral form or ionic form or a mixture thereof. Some suitable monomer (ii) include, for example, vinyl monomers with at least one acid-functional group. Independently, in some embodiments at least one monomer (ii) with a carboxylic acid group is used. In some embodiments, every monomer (ii) has a carboxylic acid group.

Suitable monomers (ii) having sulfonic acid group include, for example, 2-acrylamido-2-methylpropane sulfonic acid. Suitable monomers (ii) include, for example, acrylic acid, methacrylic acid, and mixtures thereof.

In some embodiments, monomer (ii) comprises at least one monomer that has exactly one acid-functional group.

In some embodiments, polymer (a) of the present invention does not include any polymerized unit of maleic anhydride. In some embodiments, polymer (a) of the present invention does not include any polymerized unit of any monomer with any anhydride group. In some embodiments, polymer (a) of the present invention does not include any polymerized unit of any monomer with more than one carboxyl group. In some embodiments, polymer (a) of the present invention does not include any polymerized unit of any monomer with more than one acid-functional group.

Mixtures of suitable monomers (ii) are also suitable.

The amount of polymerized units of monomer (ii) in the polymer is 1% to 30% by weight, based on the weight of the polymer. In some embodiments, the amount of polymerized units of monomer (ii) in the polymer is 2% or more; or 5% or more; or 10% or more; or 12% or more, or 14% or more, or 18% or more, or 20% or more, or 22% or more, by weight, based on the weight of the polymer.

In some embodiments, every monomer (i) that is present is a monomer that has no acid functional group. Independently, in some embodiments, every monomer (ii) that is present is a monomer that has index of refraction below 1.490. Also contemplated are embodiments in which every monomer (i) that is present is a monomer that has no acid functional group and in which every monomer (ii) that is present is a monomer that has index of refraction below 1.490.

Also contemplated are embodiments in which one or more monomer is used that has index of refraction of 1.490 or greater and also has at least one acid functional group. In such embodiments, it is contemplated to calculate the amount of polymerized units of monomers (i) and (ii) in polymer (a) by finding the total weight of polymerized units of monomers that have index of refraction of 1.490 or greater or that have at least one acid functional group or that have both index of refraction of 1.490 and at least one functional group, counting each polymerized unit once. That total weight will be 31% to 95% by weight, based on the weight of polymer (a).

Among embodiments in which one or more monomer is used that has index of refraction of 1.490 or greater and also has at least one acid functional group, some suitable such monomers are, for example, styrenesulfonic acid and substituted styrene sulfonic acids.

The polymer (a) of the present invention additionally contains polymerized units of one or more additional monomer (known herein as "monomer (iii)"). Monomer suitable as monomer (iii) is monomer that is not monomer (i) and is not monomer (ii). In some embodiments, monomer (iii) includes one or more vinyl monomer. In some embodiments, every monomer (iii) is a vinyl monomer.

Some suitable monomers (iii) include, for example, olefins, dienes, and (meth)acrylate monomers. As used herein, (meth)acrylate monomers include substituted and unsubstituted esters and amides of acrylic acid and methacrylic acid. Some suitable monomers (iii) include, for example, alkyl esters of (meth)acrylic acid, including, for example, those in which the alkyl group is linear, branched, cyclic, or a combination thereof, with 1 to 20 carbon atoms. In some embodiments, monomer (iii) includes one or more $C_1$-$C_{20}$ alkyl acrylate. In some embodiments, monomer (iii) includes one or more alkyl acrylate with 2 or more carbon atoms, or with 3 or more carbon atoms. Independently, in some embodiments, monomer (iii) includes one or more alkyl acrylate with 10 or fewer carbon atoms, or with 8 or fewer carbon atoms. In some embodiments in which one or more alkyl acrylate is used, the amount of polymerized units of alkyl acrylate monomer in the polymer is 5% or more, or 10% or more, by weight based on the weight of the polymer. Independently, in some embodiments in which one or more alkyl acrylate is used, the amount of polymerized units of alkyl acrylate monomer in the polymer is 50% or less, or 40% or less, by weight based on the weight of the polymer.

Independently, in some embodiments, monomer (iii) includes one or more $C_1$-$C_{20}$ alkyl methacrylate. In some embodiments, monomer (iii) includes one or more alkyl methacrylate with 6 or fewer carbon atoms, or with 3 or fewer carbon atoms, or with 2 or fewer carbon atoms. In some embodiments, monomer (iii) contains one or more alkyl acrylate and also contains one or more alkyl methacrylate. In some embodiments in which one or more alkyl methacrylate is used, the amount of polymerized units of alkyl methacrylate monomer in the polymer is 3% or more, or 6% or more, by weight based on the weight of the polymer. Independently, in some embodiments in which one or more alkyl methacrylate is used, the amount of polymerized units of alkyl methacrylate monomer in the polymer is 25% or less, or 12% or less, by weight based on the weight of the polymer.

Independently, some suitable monomers (iii) also include, for further example, substituted-alkyl esters of (meth)acrylic acid, which have the structure of alkyl esters of (meth)acrylic acid in which the ester group has one or more substituent group such as, for example, one or more hydroxyl group. Some suitable monomers (iii) include, for example, hydroxyalkyl esters of (meth)acrylic acid in which the alkyl group has 1 to 10 carbon atoms. In some embodiments, monomer (iii) contains one or more hydroxyalkyl ester of (meth)acrylic acid in which the alkyl group has 6 or fewer carbon atoms, or 4 or fewer carbon atoms. Some suitable hydroxyalkyl esters of (meth)acrylic acid include, for example, hydroxypropyl (meth)acrylate, hydroxyethyl(meth)acrylate, and mixtures thereof. In some embodiments in which one or more substituted-alkyl ester of (meth)acrylic acid is used, the amount of polymerized units of substituted-alkyl ester of (meth)acrylic acid in the polymer is 2% or more, or 5% or more, by weight based on the weight of the polymer. Independently, in some embodiments in which one or more substituted-alkyl ester of (meth)acrylic acid is used, the amount of polymerized units of substituted-alkyl ester of (meth)acrylic acid in the polymer is 40% or less, or 20% or less, by weight based on the weight of the polymer.

In some embodiments, monomer (iii) contains one or more alkyl acrylate, one or more alkyl methacrylate, and one or more substituted-alkyl(meth)acrylate.

In some embodiments, monomer (iii) does not contain any substituted-alkyl(meth)acrylate.

In some embodiments, the sum of the amount polymerized units of monomer (ii) plus the amount polymerized units of hydroxyalkyl esters of (meth)acrylic acid is, by weight based on the weight of the polymer, 10% or more, or 20% or more. Independently, in some embodiments, the sum of the amount of polymerized units of monomer (ii) plus the amount of polymerized units of hydroxyalkyl esters of (meth)acrylic acid is, by weight based on the weight of the polymer, 50% or less, or 40% or less.

In some embodiments, the amount of hydroxyalkyl esters of (meth)acrylic acid is 5% or less, or 0%, and the amount of monomer (ii) is 20% or more, by weight based on the weight of the polymer.

Independent of the composition of monomer (iii), the total amount in the polymer (a) of the present invention of polymerized units of all monomer or monomers (iii) is 30% to 89% by weight based on the weight of the polymer (a). In some embodiments, the total amount of polymerized units of monomer (iii) is 75% or less, or 60% or less, by weight based on the weight of the polymer (a).

Mixtures of suitable monomers (iii) are also suitable.

Examples of suitable polymers which comprises at least one monomer that has at least one acid-functional group include, without limitation: butyl acrylate/ethyl acrylate/methacrylic acid copolymers, octylacrylamide/acrylate/butylaminoethyl-methacrylate copolymers, methacryloyl ethylbetaine/methacrylate copolymers, methacrylic acid/methacrylic ester copolymer, acrylate/hydroxyester acrylate copolymers, methacrylic acid/acrylic acid ester copolymers, vinyl acetate/crotonic acid copolymers, vinyl acetate/crotonic acid/vinyl neodecanoate, acrylate copolymer, methacrylates/acrylates copolymer/amine salt, AMP-acrylates/diacetone-acrylamide copolymer, acrylate/methacrylate polymers, acrylate/acrylamide copolymers, acrylate/succinate/hydroxyacrylate copolymers, acrylates/t-butylacrylamide copolymer, acrylates/$C_{1-2}$ succinates/hydroxyacrylates copolymer, acrylamide/sodium acryloyldimethyltaurate/acrylic acid polymer and mixtures thereof.

In some embodiments, one or more chain transfer agent is used in the polymerization of polymer (a). Chain transfer agents are compounds that are effective at promoting chain transfer process during free-radical polymerization. It is contemplated that chain transfer agents act to reduce the molecular weight of the polymer that is produced by the polymerization process. Some suitable chain transfer agents include, for example, mercaptans, sulfides, and halides. Some suitable halides, for example, include alkyl halides, such as, for example, halomethanes and halogenated esters (such as, for example, halogenated acetates). Suitable sulfides include, for example, dialkyl disulfides, diaryl disulfides, diaroyl disulfides, and xanthogens. Some suitable mercaptans include, for example, unsubstituted alkyl mercaptans and substituted alkyl mercaptans. Substituted alkyl mercaptans include, for example, compounds in which one or more hydroxyl group and/or one or more carboxyl group is attached to the alkyl portion of the molecule, in addition to the one or more thiol group. In some embodiments, one or more unsubstituted alkyl mercaptan is used.

In some of the embodiments in which one or more chain transfer agent is used, the amount of chain transfer agent, in millimoles per 100 grams of total monomer, is 0.5 or more; or 1 or more; or 2 or more. Independently, in some of the embodiments in which one or more chain transfer agent is used, the amount of chain transfer agent, in millimoles per 100 grams of total monomer, is 20 or less; or 10 or less; or 5 or less.

In some embodiments, polymer (a) of the present invention does not include any polymerized unit of any monomer that is a vinyl lactam. Independently, in some embodiments, polymer (a) of the present invention does not include any polymerized unit of any monomer that is an amide of acrylic acid or an amide of methacrylic acid. Independently, in some embodiments, polymer (a) of the present invention does not include any polymerized unit of any monomer that is an amide compound. Independently, in some embodiments, polymer (a) of the present invention does not include any polymerized unit of vinyl acetate. Independently, in some embodiments, polymer (a) of the present invention does not include any polymerized unit of any monomer that has molecular weight of 500 or greater.

Independently, in some embodiments, all of the polymerized units in the polymer (a) of the present invention are selected from the group consisting of styrene, alkyl-substituted styrene, alkyl esters of (meth)acrylic acid, hydroxyalkyl esters of (meth)acrylic acid, chain transfer agents, and mixtures thereof.

Neutralization of the polymer (a) improves its compatibility with organic solvents, water, and mixtures thereof, resulting in hair styling compositions that have improved clarity. A description of methods for neutralization of acid-containing polymers is provided below within the discussion of neutralizing agents. Upon full neutralization, a polymer can have turbidity of 120 NTU or lower in a solution with 12% polymer solids (by weight based on the weight of the solution) or less. In some embodiments, polymer (a) has "enhanced clarity," which means herein that it has turbidity of 10 NTU or lower in a solution with 12% polymer solids or less (by weight based on the weight of the solution).

Compositions of the present invention are storage stable. That is, after storage in a closed container for 6 months at room temperature, there is no visible precipitate and there is no change in the turbidity. In some embodiments, there is no visible precipitate and there is no change in the turbidity after storage at room temperature for 18 months.

As used herein, compatibility of a polymer with the other ingredients in a hair styling composition may be measured by measuring the turbidity (i.e., clarity) of the composition which includes that polymer. In particular, a test solution including the polymer is made and tested for turbidity as described in the Examples section below. The composition of the test solution is comparable to the composition of a generic hair styling composition including the polymer. Upon full neutralization, a polymer is considered herein to be compatible if the test solution containing it has turbidity of 120 Nephelometric Turbidity Units (NTU) or lower in a test solution with 12% or lower polymer solids (by weight based on the weight of the solution). If the polymer has turbidity of 10 NTU or lower, in a test solution with 12% polymer solids (by weight based on the weight of the solution), it is considered to have enhanced clarity. Thus, the "compatibility" of the polymer, as is meant herein, is determined based on the polymer's performance in a test solution. The test solution has a composition equivalent to a typical hair styling composition and is analyzed and evaluated for stability, measured in NTUs, as described in detail hereinafter.

It is contemplated that, in general, when a polymer that is compatible in a particular composition according to the turbidity (clarity) test described herein, it may not be compatible with all of the components of a hair styling composition. It is possible, for example, that other properties of the polymer, such as humidity resistance, will be impacted when combined with other components of a composition. For illustration, it is useful to consider an example where a polymer alone is clear in solution, and a solution of one or more other additives to be included in the composition is also clear by the turbidity test described herein. However, the combination of the two solutions may produce a turbid composition, indicating lack of compatibility between the various components. An appropriately selected set of additives can result in a clear solution with the polymer, indicating good compatibility. The level of the additives and relative amounts may also be critical to achieve the desired level of compatibility.

In addition, the hair styling composition of the present invention contains a neutralizer. It is contemplated that polymer (a) is soluble in the hair styling composition "as is" or upon neutralization of some or all of the acid-functional groups contained in the polymer (a). Neutralization of the acid-functional groups typically aids in dissolving the polymer (a) in the hair styling composition. Furthermore, even where polymer (a) is soluble in the hair styling composition, neutralization of some or all of the acid-functional groups contained in the polymer (a) may render the polymer (a) more compatible, i.e., even more soluble, with the Volatile Organic Compounds (VOCs) present in the hair styling composition of the present invention. The description of VOCs is stated in the composition composition section. Increased solubility of the polymer (a) in the VOC-containing hair styling composition of the present invention, in turn, enhances the clarity of the composition.

In accordance with the present invention, the neutralizer comprises tetrabutylammonium hydroxide (TBAH) and aminomethyl propanol (AMP). The preferred ratio of TBAH to AMP for clarity is (i) 10% to 100% neutralization of the acid group of the polymer by tetrabutylammonium hydroxide, and (ii) 90% to 0% neutralization of the acid group of the polymer by aminomethyl propanol.

The preferred ratio of TBAH to AMP for humidity resistance is (i) 0% to 90% neutralization of the acid group of the polymer by tetrabutylammonium hydroxide, and (ii) 100% to 10% neutralization of the acid group of the polymer by aminomethyl propanol.

The optimum ratio for both clarity and humidity resistance is (i) 10% to 30% neutralization of the acid group of the polymer by tetrabutylammonium hydroxide, and (ii) 90% to 70% neutralization of the acid group of the polymer by aminomethyl propanol.

The neutralizer is present in a mole ratio of neutralizer to acid-functional groups on said polymer (a) of from 0:1 to 1.2:1. It has been noted that use of a greater proportion of TBAH than the proportion of AMP in the composition produces a hair styling composition that is unacceptably tacky.

As is familiar to persons of ordinary skill in the relevant art, the amount of neutralizer to be used in the hair styling composition may be calculated based on the acid number of the polymer (a), and it is recommended to neutralize 60%-120%, for example, 80%-100%, of the total acid in the polymer (a). This amount of neutralizer will provide improved clarity, as well as maintaining the degree of performance of the other properties in the hair styling composition. In one embodiment, the amount of neutralizer to be used, "x" in grams of neutralizer, may be calculated using the following formula:

$$x = \frac{A*B*C*D}{E*1000}$$

X=grams of neutralizing agent required,
A=millimoles acid/gram Polymer SOLIDS,
B=grams of polymer (solids) in the composition,
C=molecular weight of the neutralizing agent,
D=% neutralization desired, and In some embodiments, the neutralizer may, optionally, comprise other neutralizing compounds in addition to TBAH and AMP as described above. Such other neutralizing compounds may be selected, for example, from one or more amines, alkali or alkaline earth metal hydroxides, ammonium hydroxide, and mixtures thereof. Suitable amine neutralizers include, for example, 2 amino-2-methyl-1,3-propanediol, 2-amino-2-methyl-1-propanol, N,N-dimethyl-2-amino-2-methyl-1-propanol, mono-isopropanolamine, triisopropanolamine, ethanolamine, triethanolamine, cyclohexylamine, morpholine, and mixtures thereof. Suitable alkali or alkaline earth metal hydroxides include, for example, sodium hydroxide and potassium hydroxide. In some embodiments, the neutralizer is selected from one or more of 2-amino-2 methyl-1, 3-propanediol, 2 amino-2-methyl-1-propanol, N,N-dimethyl-2-amino-2-methyl-1-propanol, potassium hydroxide, triethanolamine, and triisopropanolamine. Mixtures of suitable neutralizing compounds are also suitable.

The present invention is not limited to any theory, it is considered that, in some embodiments, one or more neutralizer (or other compound in the composition) will be sufficiently compatible with the polymer (a) that the combination of polymer (a) and other ingredients will have improved compatibility, which provides improved composition clarity.

It is useful to characterize compositions of the present invention by the Volatile Organic Compounds (VOC) content. The VOC content of a composition is the amount of all volatile organic compounds, expressed as a percentage by weight based on the total weight of the composition. It is contemplated that, if two or more organic compounds that have normal boiling point of 250° C. or lower are used in the composition, they may or may not be mixed together prior to being added to the composition. In some embodiments, compositions of the present invention have VOC content of 30% to 95%.

In some embodiments, herein called "low-VOC" embodiments, the VOC content of the hair styling composition is between 30% and 65%. In some low-VOC embodiments, the VOC content is 45% or higher; or 50% or higher. Independently, in some low-VOC embodiments, the VOC content is 60% or lower.

It is contemplated that some low-VOC embodiments will be useful as aerosol sprays and that some low-VOC embodiments will be useful as pump sprays.

In some embodiments, herein called "high-VOC" embodiments, the VOC content of the hair styling composition is between 70% and 95%. In some high-VOC embodiments, the VOC content is 75% or higher. Independently, in some high-VOC embodiments, the VOC content is 90% or lower; or 85% or lower.

It is contemplated that some high-VOC embodiments will be useful as aerosol sprays and that some high-VOC embodiments will be useful as pump sprays.

Also contemplated are embodiments, herein called "very-low-VOC" embodiments, in which the VOC content is 0% to less than 30%. In some very-low-VOC embodiments, no propellant is used. It is contemplated that some very-low-VOC embodiments, for example, will be useful as spray gels. Some spray gels contain one or more thickener. In some spray gels in which thickener is used, the amount of thickener has weight ratio of thickener to polymer (a) of 0.05:1 to 1:1.

Among the very-low-VOC embodiments are contemplated some embodiments, herein called "extremely-low-VOC" embodiments, in which the VOC content is 0% to 1%. Some extremely-low-VOC embodiments will be useful, for example, as non-aerosol mousses, hair styling gels, hair setting lotions, and hair pomades.

Non-aerosol mousse typically contains one or more betaine surfactant, sometimes in an amount having weight ratio of betaine surfactant to polymer (a) of 0.05:1 to 1:1. Hair styling gel typically contains one or more thickener (also called rheology modifier), sometimes in an amount having weight ratio of thickener to polymer (a) of 0.05:1 to 0.5:1. Hair setting lotion typically contains one or more fatty compound (i.e., a compound containing, possibly among other chemical groups, a hydrocarbon chain of 8 or more carbon atoms), sometimes in an amount having weight ratio of fatty compound to polymer (a) of 0.1:1 to 2:1. In some hair setting lotion, the fatty compound is liquid at 20° C. Waxes are fatty compounds that are solid at 20° C. Hair pomades sometimes contain one or more wax, sometimes in an amount having weight ratio of wax to polymer (a) of 0.1:1 to 2:1.

In some embodiments, there is a tendency for the composition to form foam. In some situations, such foam is undesirable. For example, the presence of air bubbles may reduce the shininess of treated hair. Among such embodiments, it is contemplated that a silicone defoamer may, optionally, be added to the composition. If a silicone defoamer is used, the weight ratio of silicone defoamer to polymer (a) may be, for example, from 0.01:1 to 0.5:1, or from 0.05:1 to 0.15:1.

In addition to polymer (a), some compositions of the present invention contain a solvent mixture (b), which comprises one or more volatile organic solvent, water and, optionally, one or more propellant. The volatile organic solvent contained in solvent mixture (b) is known herein as "solvent (sb)." Solvent (sb) is liquid at 25° C. and is capable of dissolving polymer (a). In some embodiments, one or more solvent (sb) is used that has boiling point of 200° C. or lower, or 150° C. or lower, or 100° C. or lower. Independently, in some embodiments, one or more solvent (sb) is used that has boiling point of 30° C. or higher, or 45° C. or higher, or 60° C. or higher. In some embodiments, every organic solvent that is used in the hair styling composition is a solvent (sb). Independently, in some embodiments, every organic solvent that is used in the hair styling composition has normal boiling point of 100° C. or lower.

Some suitable solvents (sb) include, for example, hydrocarbons, which may be linear, cyclic, branched, or a combination thereof; ketones; ethers; furans; fully or partially halogenated hydrocarbons; alcohols; aromatic compounds; and mixtures thereof. In some embodiments, the solvent (sb) contains one or more alcohol. Suitable alcohols include, for example, $C_1$-$C_5$ hydrocarbons with a single hydroxy group. One suitable alcohol is ethyl alcohol.

In some embodiments, solvent (sb) is cosmetically acceptable. That is, the solvent (sb) is suitable for use in hair spray and/or cosmetics (i.e., uses that involve contact with human hair and/or skin).

Mixtures of suitable organic solvents are also suitable.

In some embodiments, no organic solvent is used in solvent mixture (b) other than one or more alcohol.

The amount of solvent (sb) in the solvent mixture (b) is, by weight, based on the weight of the solvent mixture (b), 5% to 95%. In some embodiments, the amount of solvent (sb) in solvent mixture (b) is, by weight, based on the weight of solvent mixture (b), 5% to 90%.

The amount of water in solvent mixture (b) is, by weight, based on the weight of solvent mixture (b), 5% to 95%. In some embodiments, the amount of water in solvent mixture (b) is, by weight, based on the weight of solvent mixture (b), 10% to 50%.

In some embodiments, no propellant is used in solvent mixture (b).

Among embodiments in which a composition of the present invention is intended to be used in an aerosol spray, an appropriate propellant is also used. Propellants are gaseous at 25° C. and one atmosphere pressure. Some suitable propellants have normal boiling point of 24° C. or lower; or 0° C. or lower; or −20° C. or lower. Independently, some suitable propellants have normal boiling point of −196° C. or higher; or −100° C. or higher; or −50° C. or higher.

In some embodiments, one or more organic propellant is used. In some embodiments, every propellant that is used is organic.

Independent of the boiling point at one atmosphere pressure, some propellants, called "liquefied propellants," are liquid at 25° C. inside a pressurized aerosol can. Some of such liquefied propellants are, for example, halocarbons, hydrocarbons, or mixtures thereof. Some propellants, called "compressed gas propellants," remain gaseous at 25° C. inside a pressurized aerosol can.

Some suitable propellants are, for example, alkanes having 4 or fewer carbon atoms, fluorinated hydrocarbons having 2 carbon atoms, dimethyl ether, and mixtures thereof. Some suitable propellants are, for example, n-butane, isobutane, propane, dimethyl ether, 1,1-difluoroethane, tetrafluoroethane, and mixtures thereof. In some embodiments, the propellant contains one or more of dimethyl ether, 1,1-difluoroethane, tetrafluoroethane, or any mixture thereof. In some embodiments, every propellant is selected from dimethyl ether, 1,1-difluoroethane, tetrafluoroethane, and mixtures thereof.

In some embodiments, a water-soluble propellant is used (i.e., a propellant that is soluble in water at 25° C. at autogenous pressure). The autogenous pressure is the pressure inside a sealed aerosol can that arises from the volatility of the ingredients. One suitable water-soluble propellant is, for example, dimethyl ether. In some embodiments, every propellant that is used is water-soluble. In some embodiments, the only propellant that is used is dimethyl ether.

Among some embodiments in which one or more propellant is used, the amount of propellant, by weight based on the weight of solvent mixture (b), is 25% or more; or 35% or more; or even 45% or more. Independently, among some embodiments in which one or more propellant is used, the amount of propellant, by weight, based on the weight of solvent mixture (b), is 80% or less, or 60% or less; or even 55% or less.

Among all the various embodiments of the present invention, a few illustrative but not limiting embodiments are contemplated as follows.

In one embodiment, solvent mixture (b) contains 30% to 50% water, and 50% to 70% solvent (sb), by weight based on the weight of solvent mixture (b), and no propellant.

In a second embodiment, solvent mixture (b) contains 5 to 25% water, and 75% to 90% solvent (sb), by weight based on the weight of solvent mixture (b), and no propellant.

In a third embodiment, solvent mixture (b) contains 45% to 55% propellant, 30 to 45% water, and 0% to 25% solvent (sb), by weight based on the weight of solvent mixture (b).

In a fourth embodiment, solvent mixture (b) contains 40% to 60% propellant, 5% to 25% water, and 15% to 85% solvent (sb), by weight based on the weight of solvent mixture (b).

In a fifth embodiment, solvent mixture (b) contains 40% to 60% propellant, 0% to 1% water, and 40% to 60% solvent (sb), by weight based on the weight of solvent mixture (b).

In a sixth embodiment, solvent mixture (b) contains 0% to 1% water, 99% to 100% solvent (sb), by weight based on the weight of solvent mixture (b), and no propellant.

Among embodiments employing solvent mixture (b), the amount of the polymer (a) present in the hair styling composition of the present invention is 1% to 10% by weight based on the sum of the weights of polymer (a) and solvent mixture (b). In some embodiments, the amount of polymer (a) is 2% or more, or 3% or more, or 4% or more, by weight based on the sum of the weights of polymer (a) and solvent mixture (b). In some embodiments, the amount of polymer (a) is 8% or less, or 6% or less, or 5% or less, by weight based on the sum of the weights of polymer (a) and solvent mixture (b).

Among embodiments in which one or more adjuvant is used, adjuvants may include, for example, one or more polymers other than polymer (a), one or more of preservatives (including, for example, one or more of organic acids, isothiazolones, iodopropynylbutyl carbamate, benzyl alcohol, imidazolidinylurea and alkyl parabens); thickeners; moisturizers (such as glycerine, hydrolyzed silk protein, and hydrolyzed wheat protein); conditioning agents such as panthenol; conditioning agents (U.S. Pat. No. 5,164,177 may be consulted for further general and specific details on suitable conditioning agents); emulsifiers; antistatic aids; extracts; proteins; vitamins; colorants; UV protectors; fragrances, and corrosion inhibitors. In some embodiments, no adjuvant is used.

In some embodiments in which one or more adjuvant is used, the ratio of the weight of the total amount of adjuvants to the weight of polymer (a) is 0.01:1 or higher; or 0.05:1 or higher; or 0.1:1 or higher. Independently, in some embodiments in which one or more adjuvant is used, the ratio of the weight of the total amount of adjuvants to the weight of polymer (a) is 1.4:1 or lower; or 1.2:1 or lower; or 1.1:1 or lower.

Among embodiments in which one or more polymer other than polymer (a) is used in the composition of the present invention, a polymer other than polymer (a) may be one or more hair fixative polymers such as, for example, butyl acrylate/ethyl acrylate/methacrylic acid copolymers, poly(vinyl pyrrolidone)/vinyl acetate copolymers, octylacrylamide/acrylates/butylaminoethyl-methacrylate copolymers, vinyl-caprolactam/vinyl-pyrrolidone/dimethylaminoethyl-methacrylate copolymers, methacryloyl ethyl-betaine/methacrylate copolymers, methacrylic acid/methacrylic ester copolymer, acrylates/hydroxyesters acrylates copolymer, methacrylic acid/acrylic acid ester copolymers, and polyesters. Additional hair fixative polymers that may be useful for blending with polymer (a) include, for example (by INCI name), PVP/VA copolymer, ethyl ester of PVM/MA copolymer, butyl ester of PVM/MA copolymer, vinyl acetate/crotonic acid copolymer, vinyl acetate/crotonic acid/vinyl neodecanoate, VA/butyl maleate/isobornyl acrylate copolymer, acrylates copolymer, diglycol/CHDM/isophthalates/SIP copolymer, acrylates/hydroxyester acrylates copolymer, methacrylates/acrylates copolymer/amine salt, AMP-acrylates/diacetone-acrylamide copolymer, AMPD-acrylates/diacetone-acrylamide copolymer, acrylates/methacrylate polymers, acrylates/acrylamide copolymer, PVP/vinyl caprolactam/DMAPA acrylates copolymer, polyvinylcaprolactam, isobutylene/ethylmaleimide/hydroxyethylmaleimide copolymer, acrylates/succinates/hydroxyacrylates copolymer, polyurethane-1, Octylacrylamide/Acrylates/Butylaminoethyl Methacrylate Copolymer, Vinyl caprolactam/VP/Dimethylaminoethyl Methacrylate Copolymer, Acrylates/t-Butylacrylamide Copolymer, Acrylates/C1-2 Succinates/Hydroxyacrylates Copolymer, Acrylamide/Sodium Acryloyldimethyltaurate/Acrylic Acid Polymer and mixtures thereof.

Among embodiments in which one or more polymer other than polymer (a) is used in the composition of the present invention, a polymer other than polymer (a) may be one or more rheology modifier polymers such as, for example, Acrylates Steareth-20 Methacrylate Copolymer, Acrylates Beheneth-25 Methacrylate Copolymer, Acrylates Steareth-20 Methacrylate Crosspolymer, Acrylates Copolymer, Acrylates/Vinylneodecanoate Crosspolymer, and mixtures thereof.

In some embodiments, every polymer in the hair styling composition is a polymer (a). Independently, in some embodiments, exactly one polymer (a) is used. In embodiments in which exactly one polymer (a) is used, polymer (a) will show the usual distributions around characteristics such as, for example, molecular weight, glass transition temperature, and particle size, but polymer (a) will not be a blend of two or more different polymers with distinct characteristics.

The water in the composition of the present invention may be introduced into the composition by any method. It is contemplated, for example, that water may be added directly to the composition. It is also contemplated, for example, that polymer (a) may be made by emulsion polymerization to produce a polymer latex, and that latex, containing both polymer (a) and water, may be added to the composition. Also contemplated are embodiments in which some water is added to the composition directly and some water is added as part of a polymer latex.

In some embodiments, the hair styling composition of the present invention does not contain any silicone compound. Independently, in some embodiments, the hair styling composition of the present invention does not contain any plasticizer. Independently, in some embodiments, the hair styling composition of the present invention does not contain divalent metal cations in amounts sufficient to cause crosslinking. In some embodiments, no divalent metal cations are added to the hair styling composition of the present invention. In some embodiments, no divalent metal cations are present in the hair styling composition of the present invention.

In some embodiments, the hair styling composition of the present invention is optically clear. That is, when all ingredients except for propellant (if any is to be used) are mixed together, and the resulting solution is measured for turbidity as described in the Examples below, the turbidity result is 10 NTU or lower in a solution with 12% polymer solids or less.

It is to be understood that in the present specification and claims, all operations and measurements, unless stated otherwise in specific cases, are conducted at 25° C.

EXAMPLES

In the following examples, the following terms and test procedures are used:
- BA=butyl acrylate
- MMA=methyl methacrylate
- HEMA=hydroxyethyl methacrylate
- MAA=methacrylic acid
- Sty=styrene
- BzA=benzyl acrylate
- EHA=2-ethylhexyl acrylate
- n-DDM=n-dodecyl mercaptan
- t-DDM=t-dodecyl mercaptan
- 3-MBP=3-mercapto-butyl propionate
- 15-S-40=Tergitol™ 15-S-40 secondary alcohol ethoxylate from Dow Chemical Co.
- FES-61=Disponil™ FES-61 fatty alcohol polyglycol ether sulfate, sodium salt, from Cognis Co.
- FES-77=Disponil™ FES-77 fatty alcohol ether sulfate, sodium salt, from Cognis Co.
- AMP-95=Aminomethyl propanol, from Angus Chemical Co.
- DS-4=sodium dodecylbenzensulfonate, Polystep™ A-16-22, from Stepan Co.
- RS-610=Rhodafac™ RS-610-A-25, ammonium phosphate ester from Rhodia, Inc.
- ALS=ammonium lauryl sulfate, Polystep™ B-7, from Stepan Co.

Molecular Weight

Samples were dissolved in tetrahydrofuran (THF)—2 mg solid polymer per ml of THF—shaken overnight, and filtered through a 0.45 micrometer polytetrafluoroethylene (PTFE) filter. Analysis was performed by size exclusion chromatography (SEC) using a liquid chromatograph including AGILENT™ Model 1100 isocratic pump, autosampler, degasser (all from Waldbronn, Co., Germany) and WATERS™ Model 2414 differential refractometer (Milford Co.), at 40° C. Column set contained three PLgel columns (5 micrometer, 300× 7.5 mm) connected in series, with respective pore sizes of 100, 1,000, and 10,000 Angstrom units. Injection volume was 100 microliter. Data acquisition and processing were performed using Cirrus™ Software, version 3.0, from Polymer Laboratories, UK. Molar mass data were determined via ten-point standard curve acquired from preparations of two commercially available, pre-weighed polystyrene reference mixes, using third order fitting. Reported quantities are Mw (weight-average molecular weight) and Mw/Mn (quotient obtained by dividing Mw by Mn, the number-average molecular weight). The designation "Mw (k)" means Mw divided by 1,000.

Preparation of Sample Solution at 12% Polymer Solids

Sample solution was prepared as follows. A sample of a latex or solution is neutralized with AMP-95, either by calculating the amount of AMP-95 to be equivalent to the acid groups on polymer (a) or by titrating to a pH value of 7.5. An amount of neutralized latex polymer is chosen to contain 6 grams of solid polymer. That chosen amount of neutralized latex polymer is mixed with 30.0 g ethanol and sufficient water to make the total weight of the solution 50.0 g.

Preparation of Sample Solution at 10% Polymer Solids

Same as the sample preparation at 12% (as described above) except that an amount of neutralized latex polymer is chosen to contain 5 grams of solid polymer.

Turbidity

A sample solution was placed in a vial of size 30 ml (1 ounce) and measured using HF Scientific Micro 100 Laboratory Turbidimeter, using specifications published by the United States Environmental Protection Agency as EPA method 180.1 (Nephelometric Method). Results are reported Nephelometric Turbidity Units (NTU), as T12 (turbidity in NTU of sample solution at 12% polymer solids) or T10 (turbidity in NTU of sample solution at 10% polymer solids).

A polymer is considered to have acceptable turbidity if it has T12 of 120 NTU or lower of if it has T10 of 100 NTU or lower.

A soluble surfactant is taken to be one which has less than 100 NTU haze units by this test, and shows no visible precipitate after standing for 20 minutes.

Performance evaluation was done by half-head test on Mannequin test. Each side of the mannequin heads was sprayed for similar length of time for assessment of spray properties, tackiness and dry time. Followed with assessment on stiffness, hold, shine, static, combing and residue. 3-6 experienced panelists were involved to give rating on each performance attributes.

Sample Composition
Ethanol 30-40% w/w
Water 0-10% w/w
Polymer* 2-7% w/w solids
Neutralizer (as necessary to achieve neutralization indicted in Tables 1-3 below)
Dimethyl Ether 30-60% w/w
*Polymer is selected from one of the following polymer compositions;

| Label | Lot# | Composition | Process |
|---|---|---|---|
| Acrylate Copolymer A | MDW5025 | 35STY/32BA/5EHA/ 5PEGMA/23MAA | Example 5 |
| Acrylate Copolymer B | MDW4001 | 35STY/32BA/ 5EHA/5MAA/23MAA | Example 4 |
| Acrylate Copolymer C | MDW6064 | 35STY/32BA/5EHA/ 5PEGMA/23MAA | Example 5 |

Example 1

Composition Clarity Improvement by Neutralizing Polymer with TBAH

Composition clarity was measured by Turbidimeter Micro 100 Serial No. 202230 by Scientific, Inc. (Fort Myers, Fla.). An NTU reading less than 6.0 is desired and considered as clear composition. Higher NTU values indicate hazier compositions.

TABLE 1

Composition clarity based on Acrylates copolymer A.

| Neutralizer | % neutralization | Neutralizer | % neutralization | Formulation clarity (NTU) |
|---|---|---|---|---|
| Aminomethyl propanol | 100 | | | 9.4 |

TABLE 1-continued

Composition clarity based on Acrylates copolymer A.

| Neutralizer | % neutralization | Neutralizer | % neutralization | Formulation clarity (NTU) |
|---|---|---|---|---|
| Triethylamine | 100 | | | 15.6 |
| Triisopropanolamine | 100 | | | 6.4 |
| Tributyl amine | 100 | | | 4.6 |
| Tetrabutylammonium hydroxide | 100 | | | 0.6 |
| Triisopropanolamine | 50 | Aminomethyl propanol | 50 | 6.0 |
| Tributyl amine | 50 | Aminomethyl propanol | 50 | 6.3 |
| Tetrabutylammonium hydroxide | 40 | Aminomethyl propanol | 60 | 2.3 |
| Tetrabutylammonium hydroxide | 10 | Aminomethyl propanol | 90 | 4.7 |

While using only TBAH to achieve 100% neutralization results in a hair styling composition having a very low clarity measurement of 0.6 NTU, which is highly favorable, the composition develops several undesirable properties, i.e., a strong tendency to form films, a low glass transition temperature ($T_g$), reduced humidity resistance and reduced hold.

TABLE 2

Composition clarity based on Acrylates copolymer B.

| Neutralizer | % neutralization | Neutralizer | % neutralization | Formulation clarity (NTU) |
|---|---|---|---|---|
| Aminomethyl propanol | 100 | | | 9.2 |
| Triisopropanolamine | 50 | Aminomethyl propanol | 50 | 6.4 |
| Tetrabutylammonium hydroxide | 10 | Aminomethyl propanol | 90 | 5.0 |

TABLE 3

Composition clarity based on acrylates copolymer C

| Neutralizer | % neutralization | Neutralizer | % neutralization | Formulation clarity (NTU) |
|---|---|---|---|---|
| Aminomethyl propanol | 100 | | | 6.4 |
| Tetramethylammonium hydroxide | 10 | Aminomethyl propanol | 90 | 10.6 |
| Tetraethylammonium hydroxide | 10 | Aminomethyl propanol | 90 | 11.2 |
| Tetrapropylammonium hydroxide | 10 | Aminomethyl propanol | 90 | 8.7 |
| Tetrabutylammonium hydroxide | 10 | Aminomethyl propanol | 90 | 5.6 |
| Tetramethylammonium hydroxide | 20 | Aminomethyl propanol | 80 | 12.5 |
| Tetraethylammonium hydroxide | 20 | Aminomethyl propanol | 80 | 10.1 |
| Tetramethylammonium hydroxide | 30 | Aminomethyl propanol | 70 | 11.8 |
| Tetraethylammonium hydroxide | 30 | Aminomethyl propanol | 70 | 18.2 |
| Tetramethylammonium hydroxide | 40 | Aminomethyl propanol | 60 | 11.2 |
| Tetraethylammonium hydroxide | 40 | Aminomethyl propanol | 60 | 14.7 |

It can be seen from the data provided above that, while using only AMP to achieve 100% neutralization provides a composition having a clarity measurement of 6.4 NTU, which may be marginally acceptable, addition of TBAH to the neutralizer produces a hair styling composition having an even better clarity measurement of 5.6 NTU.

TABLE 4

Composition clarity based on Acrylates/Hydroxyesters acrylates copolymer

| Neutralizer | % Neutralization | Composition Clarity (NTU) |
|---|---|---|
| AMP | 100 | 425 |
| TBAH | 100 | 9.1 |

Example 2

Addition of TBAH to Composition Already Containing Amp as Neutralizer has No Negative Impact on Performance, with Improved Shine Performance evaluation was done on mannequin heads. The hair was split in half, and each side was treated with a hair spray composition at 30 cm distance, and sprayed for 5 seconds. First, a pair of compositions having acrylates copolymer D at 5% solids level were evaluated. One formula was using AMP at 100% neutralization level as neutralizer. The other composition was using TBAH at 10% neutralization and AMP at 90% neutralization level as neutralizer. The results are presented in Table 5 below.

TABLE 5

| Attributes | Scale-1 | Scale-5 | TBAH/AMP | AMP |
|---|---|---|---|---|
| Visibility of wet particles | very visible | not visible | 4 | 4.5 |
| Dry Time | long | short | 2 | 3 |
| Tackiness | very tacky | no tack | 2 | 3 |
| Stiffness | very soft | very stiff | 4 | 3 |
| Hold | no hold | good hold | 4 | 4 |
| Shine | dull | shiny | 4 | 3 |
| Combing (large tooth) | drag | easy | 1 | 2 |
| Combing (small tooth) | drag | easy | 1 | 2 |
| Static | high | none | 4 | 4 |
| Residue | heavy | none | 4 | 4 |

Example 3

Varying the ratio of TBAH to AMP as neutralizer had a variable impact on the film humidity resistance performance of the hair styling compositions, as measured by Dynamic Mechanical Analysis. Based on the results (shown in Table 7 below), the film humidity resistance performance begins to be compromised when formulated with TBAH at 30% and AMP at 70% neutralization level. Compromised film performance is defined by the percent change in storage modulus, E', from −50° C. to 25° C. The modulus decreases from −50° C. to 25° C., therefore the percent change is negative. As discussed hereinafter, the "storage modulus decrease" is measured for a given hair styling composition at a specified relative humidity (r.h.), relative to the storage modulus of the same composition at 0% r.h. A decrease in storage modulus larger than 50%, from 0% to 30% r.h., and larger than 75%, from 0% to 60% r.h., indicates the film softens too much, resulting in poor hold and poor high humidity curl retention or high tack. Table 9 shows the change in modulus as a function of relative humidity for various ratios of TBAH to AMP.

The samples were tested on the TA Instruments Q800 Dynamic Mechanical Analyzer (DMA) using tensile film clamp fixtures. Each sample was tested from −50° C. to approximately 120° C. at a heating rate of 2 deg/min using the Temp Ramp/Freq Sweep Test in the DMA Multi-Frequency-Strain Mode. The applied frequency was 1 Hz. The Procedure Parameters were as follows: Applied Strain=0.0075%; Pre-load Force=0.01 N; and Force Track=125%. A Soak Time of 5 minutes was employed before the start of data acquisition. The dynamic storage and loss moduli (E' and E" respectively) as well as tan delta were recorded as a function of temperature. Tan delta is defined as E"/E'.

The dried strips were tested according to the protocol described above. The remaining dried strips were used to prepare samples exposed to different relative humidities. An aqueous saturated $CaCl_2$ solution was used to produce a relative humidity (RH) of approximately 30% at room temperature. A saturated aqueous solution of $NH_4NO_3$ was used to produce a relative humidity of approximately 60% at room temperature (Ref: CRC Handbook of Chemistry and Physics, $64^{st}$ Ed., CRC Press, Boca Raton, Fla., 1980, pg E-46). Petri dishes of the saturated salt solutions were placed separately in the bottoms of two desiccators. The dried films were placed in aluminum weighing boats. The boats were then placed on top of the desiccator plates and the desiccators were sealed. The films were allowed to equilibrate in the sealed desiccators for approximately 10 days before testing according to the above protocol. Consequently mechanical data was obtained on each sample in three different states: vacuum dried; at 30% RH; and at 60% RH. The results of the foregoing procedure are provided below in Table 8.

TABLE 7

Composition Description

| Composition # | Neutralizer | % Neutralization | Neutralizer | % Neutralization |
|---|---|---|---|---|
| 16EE | TBAH | 0 | AMP | 100 |
| 16EE-1 | TBAH | 10 | AMP | 90 |
| 16EE-2 | TBAH | 20 | AMP | 80 |
| 16EE-3 | TBAH | 30 | AMP | 70 |
| 16EE-4 | TBAH | 40 | AMP | 60 |

TABLE 8

Peak tan delta temperatures as a function of neutralizer composition and relative humidity.

| | 0% R.H. | | 30% R.H. | | 60% R.H. | |
|---|---|---|---|---|---|---|
| Composition | Peak tan delta T-1 | Peak tan delta T-2 | Peak tan delta T-1 | Peak tan delta T-2 | Peak tan delta T-1 | Peak tan delta T-2 |
| 16EE | | 89 | | | 34.2 | 88.1 |
| 16EE-1 | | 87.4 | 59.0 | 87.1 | 32.8 | 87.6 |
| 16EE-2 | | 85.2 | 48.1 | 85.4 | 33.2 | 85.9 |
| 16EE-3 | 66.0 | 85.4 | 41.0 | 85.2 | 29.1 | 84.1 |
| 16EE-4 | 61.5 | 82.4 | 30.2 | 85.0 | 22.5 | 84.0 |

TABLE 9

Change in storage modulus, E', as a function of relative humidity level

| | 0% rh | | | 30% rh | | | 60% rh | | |
|---|---|---|---|---|---|---|---|---|---|
| Sample | E' @ −50° C., (MPa) | E' @ 25° C., (MPa) | % change from −50 to 25° C. | E' @ −50° C., (MPa) | E' @ 25° C., (MPa) | % change from −50 to 25° C. | E' @ −50° C., (MPa) | E' @ 25° C., (MPa) | % change from −50 to 25° C. |
| 16EE-1 | 1662 | 1223 | −26.4 | 1919 | 1160 | −39.5 | 1937 | 724 | −62.6 |
| 16EE-2 | 1273 | 869 | −31.7 | 2371 | 1237 | −47.8 | 2175 | 655 | −70.0 |
| 16EE-3 | 1834 | 1232 | −32.8 | 1566 | 755 | −51.8 | 1900 | 400 | −78.9 |
| 16EE-4 | 1294 | 912 | −29.5 | 1387 | 403 | −70.9 | 1588 | 213 | −86.6 |

Example 4

Preparation of Polymer B

To a 5-liter, 4-necked round bottom flask equipped with a mechanical stirrer, thermocouple, condenser and nitrogen sparge was added 630 grams of deionized water. The reactor was purged with nitrogen and warmed to 90° C. A monomer pre-emulsion was prepared from 1077 gm of deionized water, 34.7 gm of Rhodafac RS610A25, 33.5 gm of benzoic acid powder, 14.5 gm of Disponil FES-993, 6.9 gm of n-dodecyl mercaptan (nDDM), 602.1 gm of styrene (STY), 550.5 gm of butyl acrylate (BA), 86.0 gm of 2-ethylhexyl acrylate (2-EHA), 86.0 gm of methyl methacrylate (MMA) and 387.0 gm of glacial methacrylic acid (MAA). At ~90° C. reactor temperature, the reactor was charged with a solution composed of 13.9 gm of Rhodafac RS610A25, 15 gm of deionized water, 115.5 gm of the monomer emulsion, 8.7 gm of glacial MAA and a solution composed of 1.7 gm of ammonium persulfate and 30 gm of deionized water. The reactor was held at ~88° C. for ~10 minutes. After this time, the monomer emulsion and initiator solution composed of 1.7 gm of ammonium persulfate and 226 gm of deionized water were fed over 3 hours at 15.4 and 1.3 gm/min, respectively. The reactor temperature was maintained between 87-89° C. After these additions were completed, the monomer emulsion and initiator feed lines were rinsed with 66 gm and 20 gm of deionized water, respectively. The reactor was then maintained at 88° C. for 30 minutes. After this hold had been completed, the latex was treated with the following solutions comprised of 0.023 gm of ferrous sulfate heptahydrate and 10 gm of water, 5.4 gm of t-butyl hydroperoxide and 147 gm of deionized water and 3.4 gm of Bruggolite FF-6 and 147 gm of deionized water. The reactor was cooled to 50° C. during these additions. The resulting latex was isolated and analyzed for % solids, pH, residual monomer, particle size, gel content and viscosity. Additional testing was conducted by formulating this latex to determine its composition viscosity and clarity.

Example 5

Preparation of Polymer A & C

To a 5-liter, 4-necked round bottom flask equipped with a mechanical stirrer, thermocouple, condenser and nitrogen sparge was added 645 gms of deionized water. The reactor was purged with nitrogen and warmed to 90° C. A monomer pre-emulsion was prepared from 1038 gm of deionized water, 34.6 gm of Rhodafac RS610A25, 33.4 gm of benzoic acid powder, 14.4 gm of Disponil FES-993, 3.5 gm of n-dodecyl mercaptan (nDDM), 3.5 gm of 3-MPA, 605.4 gm of STY, 588.1 gm of BA, 86.5 gm of 2-EHA, 86.5 gm of methoxy poly (ethyl glycol, Mw ~350) monomethacrylate and 388.2 gm of glacial MAA. At ~90° C. reactor temperature, the reactor was charged with a solution composed of 13.8 gm of Rhodafac RS610A25, 10 gm of deionized water, 115.2 gm of the monomer emulsion, 8.7 gm of glacial MAA and a solution composed of 1.7 gm of ammonium persulfate and 25 gm of deionized water. The reactor was held at ~88° C. for ~10 minutes. After this time, the monomer emulsion and initiator solution composed of 1.7 gm of ammonium persulfate and 225 gm of deionized water were fed over 3 hours at 15.3 and 1.2 gm/min, respectively. The reactor temperature was maintained between 87-89° C. After these additions were completed, the monomer emulsion and initiator feed lines were rinsed with 100 gm and 60 gm of deionized water, respectively. The reactor was then maintained at 88° C. for 30 minutes. After this hold had been completed, the latex was treated with the following solutions comprised of 0.022 gm of ferrous sulfate heptahydrate and 10 gm of water, 5.4 gm of t-butyl hydroperoxide and 146 gm of deionized water and 3.4 gm of Bruggolite FF-6 and 146 gm of deionized water. The reactor was cooled to 50° C. during these additions. The resulting latex was isolated and analyzed for % solids, pH, residual monomer, particle size, gel content and viscosity. Additional testing was conducted by combining this latex into a sample formulation to determine its viscosity and clarity.

We claim:

1. A hair styling composition comprising
   (a) 1% to 8% by weight of at least one polymer, based on the total weight of said polymer (a) and a solvent mixture (b), said at least one polymer comprising, as polymerized units, (i) one or more vinyl monomers, (ii) one or more monomers having at least one acid-functional group, and (iii) one or more additional monomers;
   (b) 99% to 90% by weight of said solvent mixture, based on the total weight of said polymer (a) and said solvent mixture (b), said solvent mixture comprising:
      (i) 5% to 100% by weight of at least one volatile organic solvent, based on the total weight of said solvent mixture;
      (ii) 95% to 0% by weight of water, based on the total weight of said solvent mixture, and
      (iii) 0% to 80% by weight of at least one propellant, based on the total weight of said solvent mixture; and
   (c) an amount of a neutralizer containing tetrabutylammonium hydroxide and aminomethyl propanol, said neutralizer comprising:
      (i) 10% to 30% neutralization of the acid groups of the polymer by tetrabutylammonium hydroxide, and
      (ii) 90% to 70% neutralization of the acid groups of the polymer by aminomethyl propanol;
   wherein said at least one polymer (a) has a turbidity of 6 NTU or less in a test solution with 12% or less, by weight, polymer solids, based on the total weight of the test solution.

2. The hair styling composition according to claim 1, wherein said hair styling composition has a decrease in storage modulus of no more than 50%, from 0% to 30% relative humidity.

3. The hair styling composition according to claim 1, wherein said hair styling composition has a decrease in storage modulus of no more than 75%, from 0% to 60% relative humidity.

4. The hair styling composition according to claim 1, wherein said at least one polymer (a) comprises, as polymerized units,
   (i) 30% to 75% by weight, based on the weight of said polymer, one or more vinyl monomer that has refractive index of 1.490 or higher,
   (ii) 1% to 30% by weight, based on the weight of said polymer, one or more acid-functional monomer, and
   (iii) 5% to 69% by weight, based on the weight of said polymer, one or more additional monomer.

5. The hair styling composition according to claim 4, wherein said monomer (i) comprises one or more vinyl aromatic monomer.

6. The hair styling composition according to claim 4, wherein said monomer (iii) comprises one or more hydroxyalkyl(meth)acrylate.

7. The hair styling composition according to claim 4, wherein said monomer (iii) comprises 0% to 5% hydroxyalkyl(meth)acrylate, and wherein the amount of said monomer (ii) is 20% or to 30%, by weight based on the weight of said polymer.

8. The hair styling composition according to claim 1, wherein said at least one polymer is selected from the group consisting of: butyl acrylate/ethyl acrylate/methacrylic acid copolymers, octylacrylamide/acrylate/butylaminoethylmethacrylate copolymers, methacryloyl ethyl-betaine/methacrylate copolymers, methacrylic acid/methacrylic ester copolymer, acrylates/hydroxyesters acrylates copolymer, methacrylic acid/acrylic acid ester copolymers, vinyl acetate/crotonic acid copolymer, vinyl acetate/crotonic acid/vinyl neodecanoate, acrylates copolymer, methacrylates/acrylates copolymer/amine salt, acrylates/methacrylate polymers, acrylates/acrylamide copolymer, acrylates/succinates/hydroxyacrylates copolymer, acrylates/t-butylacrylamide copolymer, acrylates/$C_{1-2}$ succinates/hydroxyacrylates copolymer, acrylamide/sodium acryloyldimethyltaurate/acrylic acid polymer, and mixtures thereof.

9. The hair styling composition according to claim 1, wherein said at least one acid-functional group is selected from the group consisting of sulfonic acid groups, carboxylic acid groups, and mixtures thereof.

10. The hair styling composition according to claim 1, wherein said propellant is present and comprises dimethyl ether.

11. A method for styling hair comprising the steps of placing said hair in a desired configuration and applying the composition of claim 1 to said hair.

* * * * *